United States Patent
Ugarov

(10) Patent No.: US 8,633,436 B2
(45) Date of Patent: Jan. 21, 2014

(54) DATA ACQUISITION MODES FOR ION MOBILITY TIME-OF-FLIGHT MASS SPECTROMETRY

(75) Inventor: Michael Ugarov, San Jose, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 207 days.

(21) Appl. No.: 13/335,059

(22) Filed: Dec. 22, 2011

(65) Prior Publication Data
US 2013/0161506 A1 Jun. 27, 2013

(51) Int. Cl.
*H01J 49/00* (2006.01)

(52) U.S. Cl.
USPC .......................... 250/282; 250/286; 250/281

(58) Field of Classification Search
USPC ............... 250/282, 290, 281, 294, 288, 292
See application file for complete search history.

(56) References Cited

U.S. PATENT DOCUMENTS

| | | | |
|---|---|---|---|
| 5,396,065 A | 3/1995 | Myerholtz et al. | |
| 5,719,392 A | 2/1998 | Franzen et al. | |
| 6,300,626 B1 | 10/2001 | Brock et al. | |
| 6,683,299 B2 | 1/2004 | Fuhrer et al. | |
| 6,900,431 B2 * | 5/2005 | Belov et al. | 250/282 |
| 7,077,944 B2 | 7/2006 | Clemmer | |
| 7,388,197 B2 * | 6/2008 | McLean et al. | 250/293 |
| 7,745,780 B2 * | 6/2010 | McLean et al. | 250/282 |
| 8,013,290 B2 * | 9/2011 | Rather et al. | 250/281 |
| 2004/0183007 A1 * | 9/2004 | Belov et al. | 250/287 |
| 2005/0001163 A1 * | 1/2005 | Belov et al. | 250/290 |
| 2008/0185513 A1 * | 8/2008 | Belov et al. | 250/288 |
| 2009/0101810 A1 * | 4/2009 | McLean et al. | 250/282 |
| 2009/0294644 A1 * | 12/2009 | Belov | 250/282 |
| 2009/0294647 A1 * | 12/2009 | Michelmann | 250/282 |

OTHER PUBLICATIONS

Brenton et al., "Improvement of the duty cycle of an orthogonal acceleration time-of-flight mass spectrometer using ion gates," Rapid Commun. Mass Spectrom. 2007; 21: 3093-3102.

* cited by examiner

*Primary Examiner* — Nikita Wells
*Assistant Examiner* — Johnnie L Smith

(57) ABSTRACT

Methods, apparatus and systems for acquiring spectrometric data from analyte ions implement a combination of drift-type ion mobility (IM) separation and time-of-flight mass spectrometry (TOF MS). Both separation techniques are carried out in tandem while applying mass filtering with a wide window of ion isolation. One mode of operation entails utilizing a mass filter to limit ion packets to ions in a selected m/z range that remains constant over the entire course of data acquisition. Another mode entails utilizing the mass filter to limit ion packets to an m/z range that varies over the course of data acquisition.

20 Claims, 9 Drawing Sheets

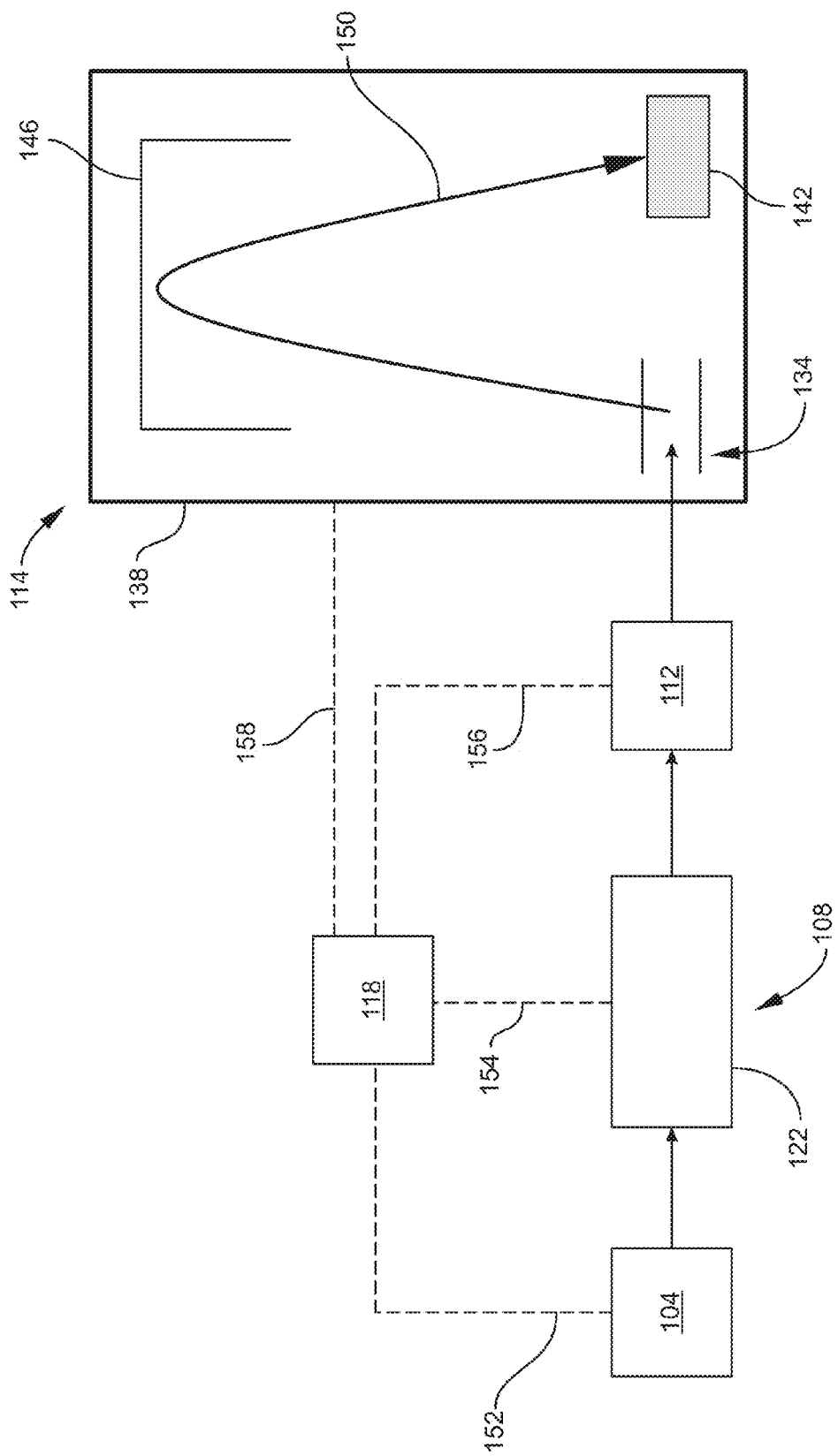

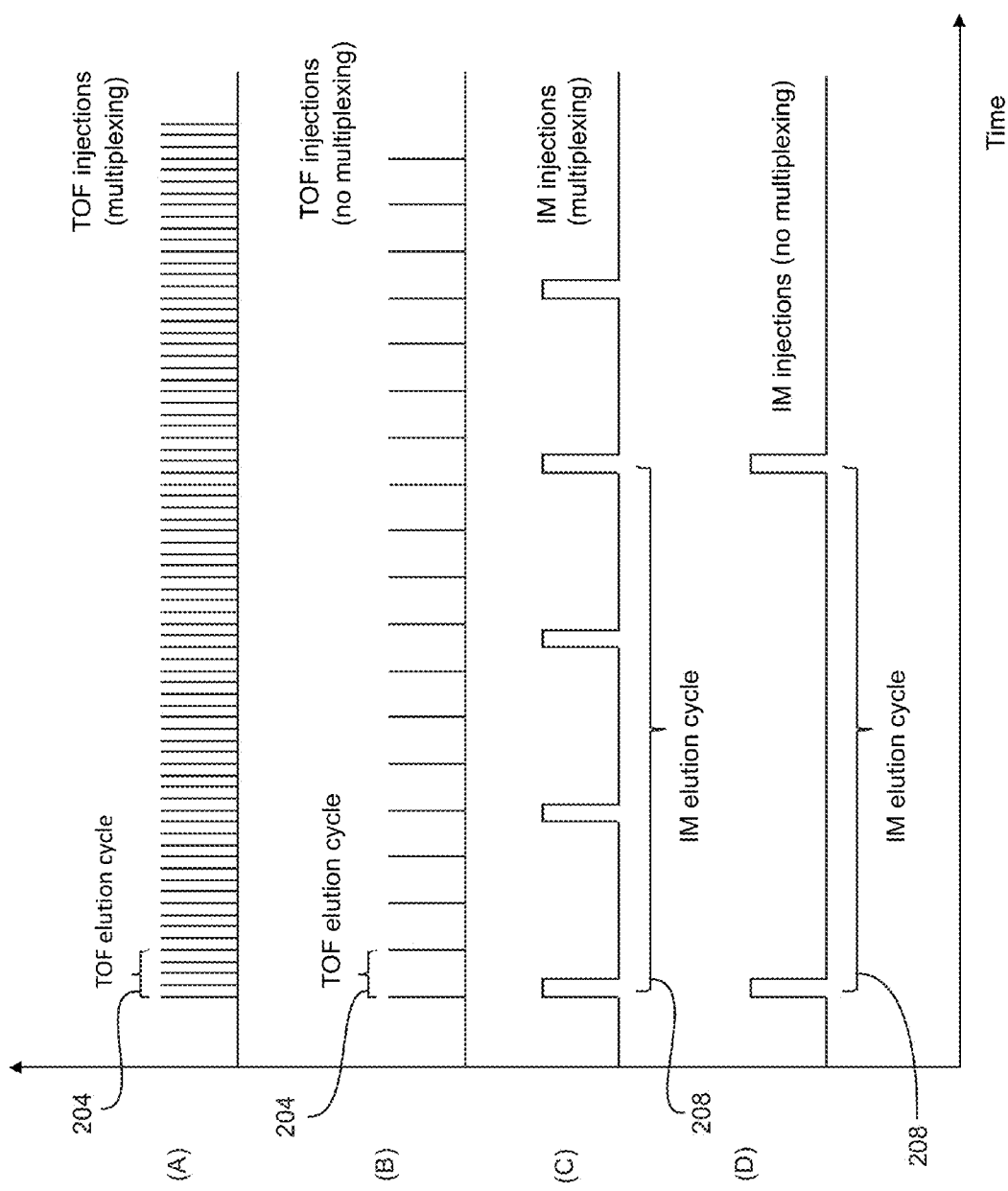

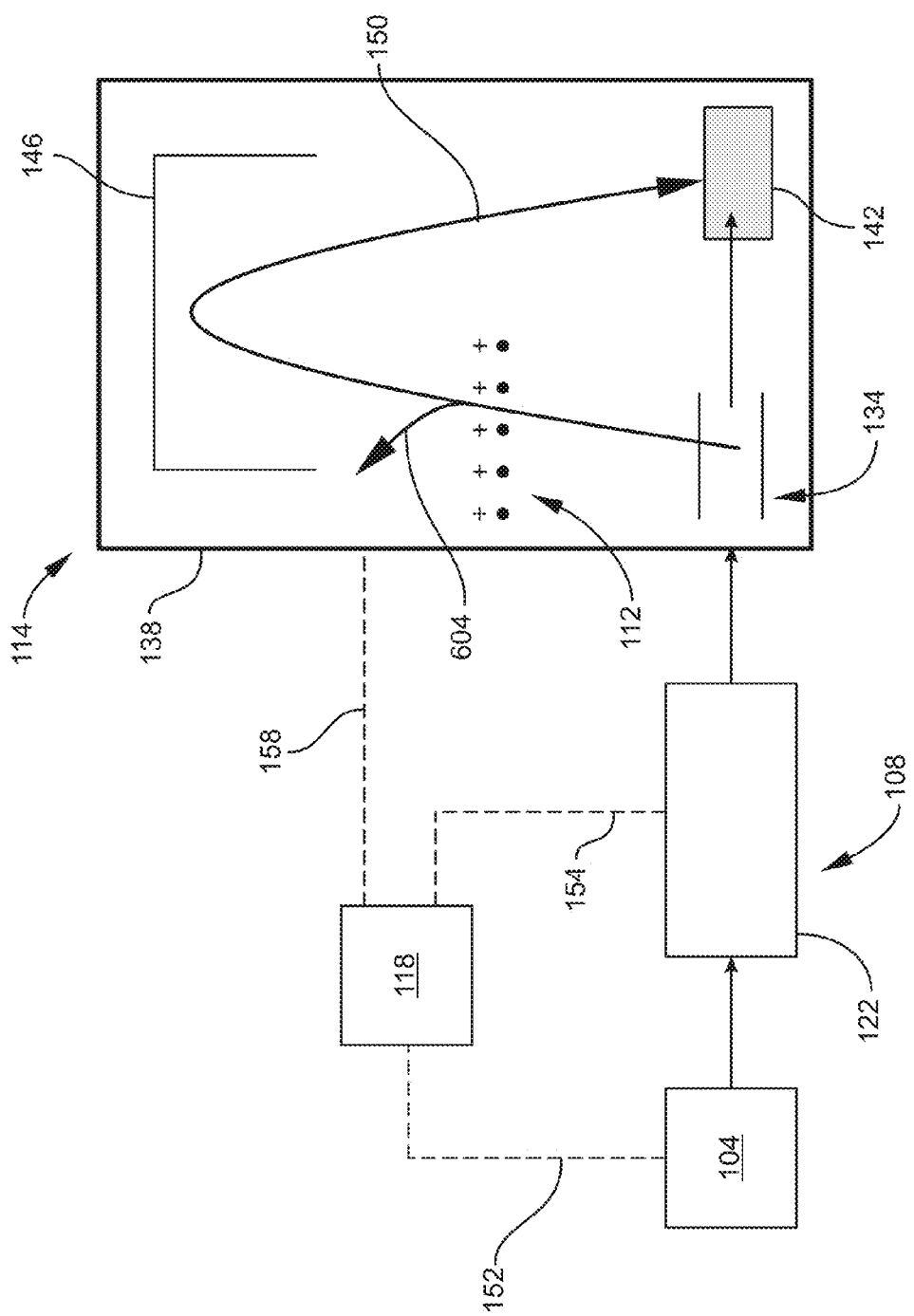

DATA ACQUISITION MODES FOR ION MOBILITY TIME-OF-FLIGHT MASS SPECTROMETRY

TECHNICAL FIELD

The present invention relates generally to acquisition of spectrometric data utilizing ion mobility separation combined with time-of-flight mass spectrometry, and more specifically to data acquisition that does not require complex deconvolution of spectra.

BACKGROUND

A drift-type ion mobility (IM) spectrometer may be coupled with a time-of-flight mass spectrometer (TOF MS) to provide unique two-dimensional information about an analyte in question. In the combined IM-TOF system, ions are separated by mobility prior to being transmitted into the TOF MS where they are mass-resolved based on their flight times to the detector. Performing the two separation techniques in tandem is particularly useful in the analysis of biopolymers such as polynucleotides, proteins, carbohydrates and the like, as the added dimension provided by the IM separation may help to mass-resolve large ions that are different from each other but present overlapping mass peaks.

While both IM and TOF MS are fast separation techniques and have typical timing parameters that make them generally compatible with each other, both techniques are inherently associated with a low duty cycle when conventionally implemented with a "pulse and wait" (or "inject and wait") approach. In the pulse and wait approach, after an ion packet is injected into the drift tube of an IM spectrometer, the next ion packet is not injected until elution the first ion packet from the drift tube is complete, which may take several hundreds of milliseconds. In a TOF MS, under the pulse and wait approach a TOF injection pulse is not applied until the slowest ion from the previous injection pulse has reached the detector. The pulse and wait approach is conventionally done to avoid spectral overlap and thereby simplify the construction of the mass spectrum from the sample under investigation, but as already noted results in a low duty cycle.

In the combined IM-TOF system the ions eluting from the IM drift tube are transmitted into the pulser of the TOF MS, which injects the ions into the flight tube of the TOF MS. Ion flight times through the flight tube to the detector are on the order of microseconds, and often two or three orders of magnitude faster than drift times through the IM drift tube. The pulser needs to operate at a higher frequency than that of the pulse and wait approach to provide an acceptable level of detection sensitivity and avoid losing an excessive amount of ions (i.e., ions transmitted through the pulser without being injected into the flight tube of the TOF MS). The overall duty cycle of the combined IM-TOF system may be improved by "multiplexing" or "oversampling" the IM instrument (i.e., injecting ion packets into the IM drift tube at a faster rate than the total elution time of each ion packet) as well as "multiplexing" or "overpulsing" the TOF MS (i.e., injecting ion packets into the flight tube of the TOF MS at a faster rate than the total flight time of each ion packet). Multiplexing can increase sensitivity and throughput and reduce the loss of ions, but conventionally requires complex deconvolution techniques (e.g., Fourier transform techniques, Hadamard transform techniques, pseudo-random sequencing, etc.) of both the IM and TOF spectra to recover the full data and generate a meaningful mass spectrum. Double (IM and TOF) spectrum deconvolution may require costly electronics and significant real-time computational resources.

Therefore, there is a need for providing a solution for implementing ion mobility time-of-flight mass spectrometry that maximizes sensitivity without involving the complications of double spectrum deconvolution.

SUMMARY

To address the foregoing problems, in whole or in part, and/or other problems that may have been observed by persons skilled in the art, the present disclosure provides methods, processes, systems, apparatus, instruments, and/or devices, as described by way of example in implementations set forth below.

According to one embodiment, a method for acquiring spectrometric data includes injecting a plurality of ion packets sequentially into an ion mobility (IM) drift tube at a multiplexed injection rate, such that at least two ion packets are present in the IM drift tube at the same time; separating ions in each ion packet according to IM as the ions drift through the IM drift tube; transmitting the ion packets into a pulser of a time-of-flight (TOF) mass spectrometer; extracting a plurality of new ion packets sequentially from the pulser into a flight tube of the TOF mass spectrometer, wherein extraction is performed at a multiplexed extraction rate such that more than one extracted ion packet is produced from the same ion packet transmitted into the pulser, and at least two extracted ion packets are present in the flight tube at the same time; separating ions in each extracted ion packet according to TOF as the ions drift through the flight tube; detecting ions as the ions arrive at a detector from the flight tube; and before detecting the ions, isolating the ions in each ion packet to a selected mass range, wherein each ion packet in the flight tube comprises ions of the same selected mass range as the ions of the other ion packets, and overlap between sequential ion packets in the flight tube is minimized.

According to another embodiment, a method for acquiring spectrometric data includes injecting an ion packet into an ion mobility (IM) drift tube; separating ions in the ion packet according to IM as the ions drift through the IM drift tube; transmitting the ion packet into a pulser of a time-of-flight (TOF) mass spectrometer; extracting a plurality of new ion packets sequentially from the pulser into a flight tube of the TOF mass spectrometer, wherein extraction is performed at a multiplexed extraction rate such that more than one extracted ion packet is produced from the same ion packet transmitted into the pulser, and at least two extracted ion packets are present in the flight tube at the same time; separating ions in each extracted ion packet according to TOF as the ions drift through the flight tube; detecting ions of the TOF-separated ion packets as the ions arrive at a detector of the TOF mass spectrometer; and before detecting the ions, isolating the ions in each ion packet to successive mass ranges, wherein each successive mass range is a higher mass range than the preceding mass range, and each mass range has a width selected to minimize overlap between sequential ion packets in the flight tube.

In some embodiments, after separating ions in each ion packet according to IM, the ions are isolated by transmitting the ion packets through a mass filter, wherein the ion packets transmitted into the pulser are mass-filtered ion packets.

In some embodiments, after extracting the ion packets from the pulser, the ions are isolated by transmitting the ion packets through a mass filter positioned in the drift tube.

Other devices, apparatus, systems, methods, features and advantages of the invention will be or will become apparent to one with skill in the art upon examination of the following figures and detailed description. It is intended that all such additional systems, methods, features and advantages be included within this description, be within the scope of the invention, and be protected by the accompanying claims.

BRIEF DESCRIPTION OF THE DRAWINGS

The invention can be better understood by referring to the following figures. The components in the figures are not necessarily to scale, emphasis instead being placed upon illustrating the principles of the invention. In the figures, like reference numerals designate corresponding parts throughout the different views.

FIG. 1 is a schematic view of an example of an ion mobility time-of-flight mass spectrometer (IM-TOF MS) that may be utilized in the implementation of methods described herein.

FIG. 2 illustrates typical timing sequences for (A) time-of-flight injections into a flight tube of an IM-TOF MS such as illustrated in FIG. 1 when multiplexing is employed, (B) time-of-flight injections without multiplexing, (C) injections into an ion mobility drift tube of the IM-TOF MS when multiplexing is employed, and (D) injections into the ion mobility drift tube without multiplexing.

FIG. 6 is a schematic view of another example of an IM-TOF MS that may be utilized in the implementation of methods described herein.

DETAILED DESCRIPTION

Figure 3A:
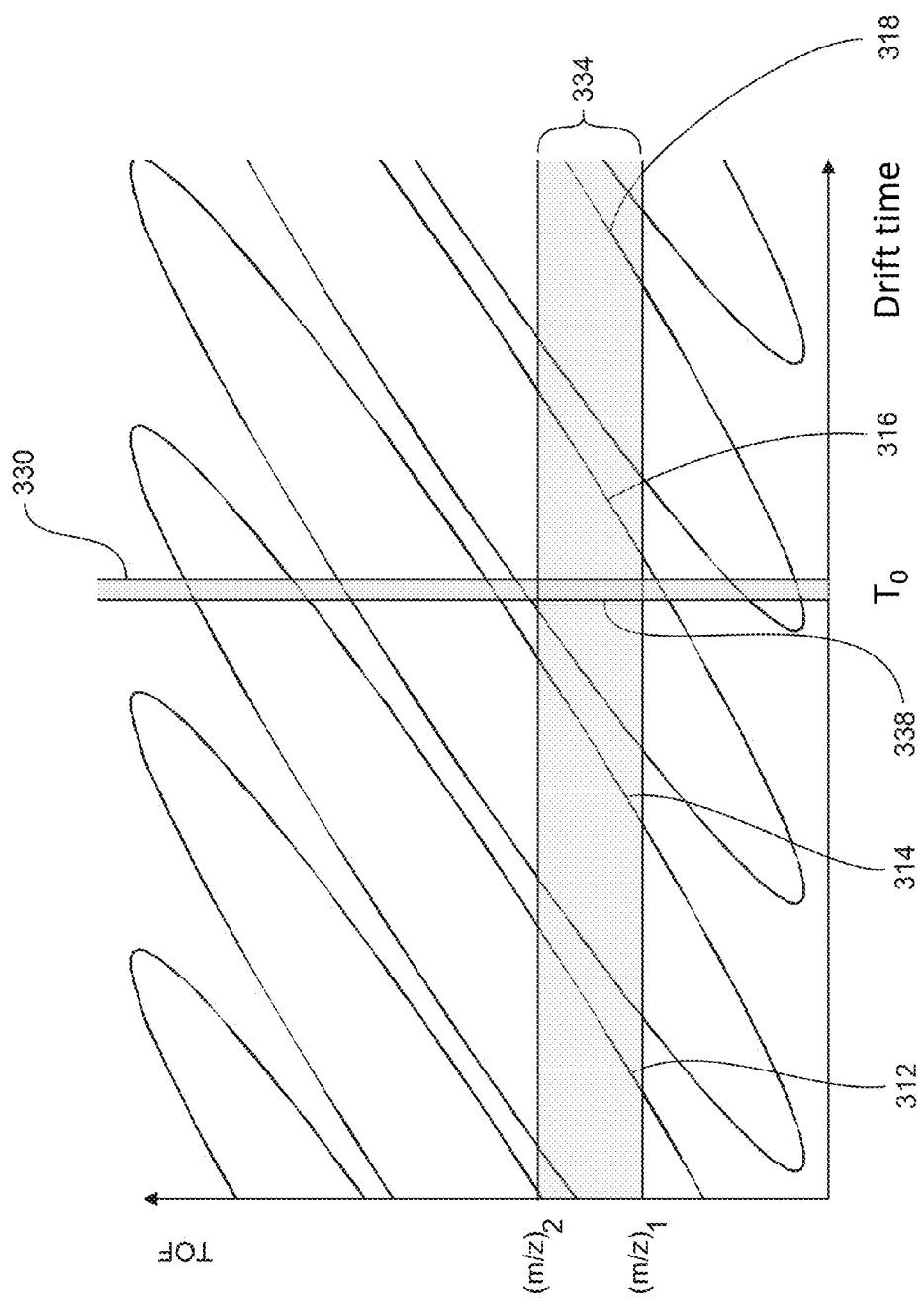
FIG. 3A is an example of a raw two-dimensional (2D) spectrum that may be acquired when IM injections are occurring at a high-frequency (multiplexed) injection rate but without multiplexing the TOF extractions.

The present disclosure describes methods, apparatus and systems for acquiring spectrometric data from analyte ions. The methods, apparatus and systems implement a combination of drift-type ion mobility (IM) separation and time-of-flight mass spectrometry (TOF MS). The methods, apparatus and systems may enable the use of the full sensitivity potential of both separation techniques in tandem by applying mass filtering with a relatively wide window (or range) of ion isolation. Examples of embodiments are described below in conjunction with FIGS. 1-7. The embodiments include at least two modes of operation. One mode entails utilizing a mass filter to limit ion packets to ions in a selected m/z range (or "mass" range) that remains constant over the entire course of data acquisition. Another mode entails utilizing a mass filter to limit ion packets to a m/z range that varies over the course of data acquisition.

FIG. 1 is a schematic view of an example of a hybrid (or tandem, or combined) ion mobility time-of-flight mass spectrometer (IM-TOF MS) system 100 that may be utilized in the implementation of methods described herein. The IM-TOF MS system 100 generally includes an ion source 104, an IM spectrometer 108, a mass filter 112, a TOF MS 114, and a system controller 118. It will be noted that the operation and design of the components of IM and TOF MS systems are generally known to persons skilled in the art and thus need not be described in detail herein. Instead, certain components are briefly described herein to facilitate an understanding of the methods presently disclosed.

The ion source 104 may be any type of continuous-beam or pulsed ion source suitable for IM and TOF operations. Examples of ion sources 104 typical for IM and TOF include, but are not limited to, electrospray ionization (ESI) sources, laser desorption ionization (LDI) sources, and matrix-assisted laser desorption ionization (MALDI) sources. In some embodiments the ion source 104 may include, or be in communication with, an ion accumulating (or ion storage) device such as an ion trap or ion optics device (not shown).

The IM spectrometer 108 includes an IM drift tube 122 with one or more ports for routing a buffer gas into the drift tube 122 in counterflow to the flight of ions through the IM drift tube 122. The IM drift tube 122 may be enclosed in a housing (not shown) that communicates with a pump (not shown) for controlling the pressure in the drift tube 122. The IM spectrometer 108 may also include a heating device (not shown) for controlling the temperature in the drift tube 122. A series of electrodes (such as ring-shaped electrodes, not shown) are typically mounted at the inside surface of the IM drift tube 122 and axially distributed along the longitudinal axis of the IM drift tube 122. The electrodes are in signal communication with a voltage source to establish a constant electric field along the longitudinal axis of the IM drift tube 122, although in some embodiments the electric field may be varied.

The mass filter 112 may be any type of mass filter suitable for providing adjustable, wide m/z ranges—or windows of ion isolation (isolation windows)—in accordance with the present teachings. In the present context, a "wide" m/z range or isolation window is typically on the order of tens to several hundreds. Examples of mass filters 112 suitable for implementing the methods presently disclosed herein include, but are not limited to, multi-pole mass filters and certain ion optics devices such as Bradbury-Nielsen gates (or grids, or shutters), or devices similar in design or operating principle to Bradbury-Nielsen gates. When the mass filter 112 is positioned as shown in FIG. 1, the multi-pole configuration is presently contemplated as being the more typical embodiment. As appreciated by persons skilled in the art, a multi-pole mass filter typically includes a set of parallel elongated electrodes elongated in the direction of ion beam transmission. The multi-pole mass filter typically has a quadrupole configuration (four electrodes), but alternatively may have a greater number of electrodes (e.g., hexapole, octopole, etc.). One or more voltage sources apply an RF voltage 180 degrees out of phase to alternating pairs of electrodes, and also apply a DC voltage to the electrodes. The m/z range to which ions are isolated by the multi-pole mass filter is selected and controlled by setting (or adjusting) the amplitude and frequency of the RF voltage and the amplitude of the DC voltage. The alternative case of a Bradbury-Nielsen gate or similar device is described below.

The TOF MS 114 includes an ion pulser (or ion extraction region) 134, a flight tube 138, and an ion detector 142. The ion pulser 134 includes a set of electrodes (e.g., grids or apertured plates) communicating with voltage sources for applying a pulsed electric field sufficient to extract ions from the ion pulser 134 into the flight tube 138. The flight tube 138 defines an electric field-free drift region through which ions drift toward the detector 142. The detector 142 may be any detector suitable for use in the TOF MS, a few non-limiting examples being an electron multiplier with a flat dynode and a microchannel plate detector. The detector 142 detects the arrival of ions (or counts the ions) and produces representative ion detection signals. In the present example, the TOF MS 114 is arranged as an orthogonal TOF MS—that is, the direction in which ions are extracted and drift through the flight tube 138 is generally orthogonal (or at least at an appreciable angle) to the direction in which ions are transmitted into the ion pulser 134. In other examples, the TOF MS 114 may be on-axis with the IM drift tube 122 and mass filter 112. Also in the present example, the TOF MS 114 includes a single- or multi-stage ion reflector (or reflectron) 146 that turns the path of the ions generally 180 degrees to focus their kinetic energy before their arrival at the detector 142, as appreciated by persons skilled in the art. The resulting ion flight path in this example is generally indicated at 150. In other embodiments, the reflector 146 is not utilized and the ion pulser 134 and detector 142 are located at opposite ends of the flight tube 138.

The system controller 118 is schematically depicted in FIG. 1 as representing one or more modules configured for controlling, monitoring and/or timing various functional aspects of the IM-TOF MS system 100, such as operation of the ion source 104, injection of ion packets into the IM drift tube 122 at a desired injection frequency, application of voltages to the electrodes of the IM drift tube 122 to establish an electric field of desired magnitude, introduction of a buffer gas and control of gas pressure (and optionally temperature) in the IM drift tube 122, setting and adjustment of the operating parameters of the mass filter 112 to select a desired m/z range, application of voltages to the ion pulser 134 at a desired pulsing (or extraction) frequency, and control of any other ion optics not specifically shown in FIG. 1. The system controller 118 is also configured for receiving the ion detection signals from the detector 142, calculating times of flight of the detected ions (e.g., utilizing a time-to-digital converter or fast analog-to-digital converter), correlating times of flight with m/z values, and performing other tasks relating to data acquisition and signal analysis as necessary to generate a mass spectrum characterizing the sample under analysis. The system controller 118 may include a computer-readable medium that includes instructions for performing any of the methods disclosed herein. For these purposes, the system controller 118 is schematically illustrated as being in signal communication with one or more components of the ion source 104, the IM spectrometer 108, the mass filter 112, and the TOF MS 114 via respective communication links 152, 154, 156, 158. A given communication link 152, 154, 156, 158 may be wired or wireless as appropriate. Also for these purposes, the system controller 118 may include one or more types of hardware, firmware and/or software, as well as one or more types of memories and databases. The system controller 118 typically includes a main electronic processor providing overall control, and may include one or more electronic processors configured for dedicated control operations or specific signal processing tasks. The system controller 118 also schematically represents all voltage sources, timing controllers, clocks, frequency generators and the like as needed for applying voltages to various components of the IM-TOF MS system 100.

The system controller 118 may also be representative of one or more types of user interface devices, such as user input devices (e.g., keypad, touch screen, mouse, and the like), user output devices (e.g., display screen, printer, visual indicators or alerts, audible indicators or alerts, and the like), a graphical user interface (GUI) controlled by software, and devices for loading media readable by the electronic processor (e.g., logic instructions embodied in software, data, and the like). The system controller 118 may include an operating system (e.g., Microsoft Windows® software) for controlling and managing various functions of the system controller 118. One or more components of the system controller 118 may be located remotely from the IM-TOF MS system 100 and communicate with the local portion of the system controller 118 over a wired or wireless communication link.

To produce a mass spectrum, the system controller 118 may include software configured for deconvoluting or otherwise mathematically reconstructing the mass spectrum in a case where the IM spectral information is convoluted. Conventionally, such software is also configured for deconvoluting the mass spectrum from convoluted mass spectral information. However, as will become evident from the description below, the methods disclosed herein do not require double (IM and TOF) spectrum deconvolution.

In operation, individual packets of ions (or ion packets) are injected sequentially into the IM drift tube 122. In some embodiments, the injection rate (or injection frequency) is a multiplexed injection rate. In the present context, a multiplexed injection rate refers to an injection rate fast enough that at a given moment after injections commence at least two sequential (or adjacent) ion packets (and typically more than two ion packets) are present in the IM drift tube 122 simultaneously. The multiplexing of the IM spectrometer 108 may also be referred to as oversampling. As the ions in each ion packet travel through the IM drift tube 122 under the influence of the applied electric field, they collide with the buffer gas molecules. Ions with relatively larger collision cross-sections are slowed down more by this process than are ions with relatively smaller collision cross-sections. Accordingly, ions with relatively smaller collision cross-sections have a higher mobility than ions with relatively larger collision cross-sections, and thus are eluted from the exit end of the IM drift tube 122 first and are sequentially followed by ions of successively lower mobilities. Thus, as each ion packet moves through the IM drift tube 122, the ion packet becomes spatially dispersed along the longitudinal axis of the IM drift tube 122 because the ions in the ion packet separate in time as a function of their differing mobilities. The resulting IM-separated ion packets are sequentially eluted from the IM drift tube 122 and transmitted into the mass filter 112. In some implementations, two or more sequential (or adjacent) ion packets may at least partially overlap before the leading ion packet is completely eluted from the IM drift tube 122. That is, the fastest ions of the preceding ion packet may overtake the slowest ions of the leading ion packet.

As each IM-separated ion packet travels through the mass filter 112 it is subjected to a composite RF/DC electric field established by the above-noted RF and DC voltages, which establish the low and high m/z cut-off values defining the selected m/z range. Ions falling outside of the selected m/z range are eliminated from each ion packet, thereby isolating the ions falling within the selected m/z range. As a result, the ion packets exiting the mass filter 112 retain their IM-based separation but now are also mass filtered in accordance with the selected m/z range. According to the present teachings, the mass filter 112 is operated to establish a much wider isolation window than is conventionally done when employing mass filters in ion processing techniques. As noted above, the width of the isolation window may be on the order of tens to several hundreds of m/z units, i.e., the width may range from about 10 to one or more hundreds. Thus, in some embodiments, the mass filter 112 may be operated to provide an isolation window having a width on the order of tens (e.g., 10, 20, 30, 40, or wider, i.e., up to 100). As an example, the selected m/z range may have a width of 30. Assuming the low m/z cut-off value is 2000, the selected m/z range in this example would be 2000 to 2030 (i.e., only ions having masses falling within the range of 2000 to 2030 would be transmitted by the mass filter 112). As another example, the selected m/z range may have a width of 60. Assuming again the low m/z cut-off value is 2000, the selected m/z range in this example would then be 2000 to 2060. In other embodiments, the mass filter 112 may be operated to provide an isolation window having a width on the order of hundreds of (e.g, 100, 200, 300, 400, or wider). As an example, the selected m/z range may have a width of 100. Continuing with the example of the low m/z cut-off value being 2000, the selected m/z range in this example would be 2000 to 2100. As another example, the selected m/z range may have a width of 200. Again taking the low m/z cut-off value to be 2000, the selected m/z range in this example would then be 2000 to 2200.

As additional examples, the width of the isolation window (or width of the m/z range)—that is, the range from the lowest mass to highest mass of ions allowed to be transmitted—may be 10-20 (e.g., the ions allowed to be transmitted might be those having masses ranging from 62-71, or 262-275, or 1262-1278, or 5462-5473, etc.); 20-30 (e.g., ions of masses from 62-81, or 262-287, or 1262-1284, or 5462-5486, etc. are transmitted); 30-40 (e.g., ions of masses from 62-92, or 262-299, or 1262-1298, or 5462-5493, etc.); 40-50; 50-60; 60-70; 70-80; 80-90; 90-100; 100-200 (e.g., ions of masses from 62-161, or 262-378, or 1262-1398, or 5462-5612, etc.); 200-300 (e.g., ions of masses from 62-261, or 262-493, or 1262-1523, or 5462-5670, etc.); 300-400; 400-500; 500-600; 600-700; 700-800; 800-900; 900-1000; 1000-2000; 2000-3000; 3000-4000; 4000-5000; 5000-6000; 6000-7000; 7000-8000; 8000-9000; 9000-10000; 10000-20000; etc. It will be understood that the low mass cut-off values of 62, 262, 1262 and 5462 provided in the foregoing examples were arbitrarily selected; the mass filtering performed in the presently disclosed methods may be applied to ions of any mass of analytical interest in the system, including larger ions of masses in the range of tens of thousands. In some embodiments of the present invention, the isolation window may allow a percentage of the m/z range expected at a given time to pass, such as 95%, 90%, 85%, 80%, 75%, 70%, etc. For example, if at a given time, the ion pulser would receive ions with m/z ranging from 100 to 120, and the mass filter is set to allow ions of 90% of the m/z range to pass, the "passing" m/z range may be 101 to 118, 102 to 119, etc. The passing m/z range may be at the middle of the expected m/z range for the given time (100-120 in the example above).

In the first mode of operation disclosed herein, each ion packet is subjected to the same mass filtering parameters—that is, the selected m/z range is the same for all ion packets. The effect of the wide mass filtering is to enable the TOF MS 114 to be multiplexed to increase sensitivity while significantly simplifying data acquisition, as described further below.

Each IM-separated, mass filtered ion packet is transmitted from the mass filter 112 into the ion pulser 134 of the TOF MS 114. The ion pulser 134 is operated to sequentially extract ions from each ion packet arriving in the ion pulser 134, thereby sequentially accelerating ion packets into the flight tube 138. More than one ion packet may be extracted from a given single IM-separated ion packet arriving in the ion pulser 134. In the present embodiment, the extraction or pulse rate (or frequency) is a multiplexed extraction rate. In the present context, a multiplexed extraction rate refers to an extraction rate fast enough that at any given moment after extractions commence at least two sequential (or adjacent) ion packets (and typically more than two ion packets) are present in the flight tube 138 at the same time. Hence, the ion packets extracted into the flight tube 138 may be characterized as being "new" or "different" in relation to the ion packets eluted from the IM drift tube 122, insofar as the extracted ion packets do not necessarily consist of the same ensemble of ions as the IM-eluted ion packet from which the extractions were taken. The multiplexing of the TOF MS 114 may also be referred to as multipulsing or overpulsing. The ions in each extracted ion packet are accelerated such that they all have the same kinetic energy, but the velocities of individual ions will differ in dependence on their individual m/z ratios. Consequently, as each extracted ion packet travels through the flight tube 138 it becomes spatially and temporally dispersed. The detector 142 counts the ions as they arrive at the detector 142 and produces an ion detection signal from which the times of flight of the ions can be calculated and correlated with their m/z ratios and a mass spectrum can be generated. As noted elsewhere, due to the mass filtering applied to the ion packets, the m/z range of the ion packets is confined, and the dispersion or spread of the ion packets is consequently limited such that little or no overlap among sequential ion packets occurs in the flight tube 138, greatly simplifying data acquisition and analysis.

FIG. 2 illustrates typical timing sequences for (A) TOF injections (extractions of ion packets from the ion pulser 134 into the flight tube 138) when multiplexing is employed, (B) TOF injections without multiplexing, (C) injections into the IM drift tube 122 when multiplexing is employed, and (D) IM injections without multiplexing. The typical duration of a full TOF elution cycle for a single ion packet is indicated at 204 in FIGS. 2(A) and 2(B). The TOF elution cycle 204 corresponds to the time it takes for the slowest (heaviest) ion of the ion packet to reach the detector 142 after extraction of the ion packet from the ion pulser 134. The typical duration of a full IM elution cycle for a single ion packet is indicated at 208 in FIGS. 2(C) and 2(D). The IM elution cycle 208 corresponds to the time it takes for the slowest (least mobile) ion of the ion packet to elute from the IM drift tube 122 after injection of the ion packet into the IM drift tube 122. When multiplexing is not employed, FIGS. 2(B) and 2(D) are respectively representative of the TOF MS 114 and IM spectrometer 108 being operated under "pulse and wait" conditions, under which the time between injections into the IM drift tube 122 may roughly correspond to the IM elution cycle 208 and the time between TOF extraction pulses may roughly correspond to the TOF elution cycle 204.

The time scale of the IM elution cycle 208 is typically a few (e.g., two or three) orders of magnitude slower than the time scale of the TOF elution cycle 204. For instance, the IM elution cycle 208 may vary in the range of 10 to 100 ms, whereas the corresponding TOF elution cycle 204 may vary in the range of 50 to 500 μs. It can be seen that without multiplexing the duty cycle is very low. Moreover, ions are lost without multiplexing because, while as noted above an ion accumulation device may employed upstream of the IM drift tube 122 to accumulate ions between injections, in the TOF MS 114 the ions that fly through the ion pulser 134 between the extraction pulses are lost. As shown in FIGS. 2(A) and 2(C), respectively, multiplexing the TOF MS 114 entails pulsing at a rate (frequency) faster than a single TOF elution cycle 204, and multiplexing the IM spectrometer 108 entails injecting at a rate (frequency) faster than a single IM elution cycle 208. In addition to improving the duty cycle, the IM spectrometer 108 may be multiplexed in a case where the ion accumulating device has limited capacity. In this case, if the ion signal is strong the ion accumulating device may become overfilled between normal injections (injections at a non-multiplexed rate), which may lead to the loss of ions and IM separation resolution. Also, multiplexing may increase the dynamic range of the instrument. When ions of the same kind are packed into very few discrete peaks, the data acquisition may become saturated. This problem may be mitigated by multiplexing, which results in the ions being spread among multiple peaks.

FIG. 3A is an example of a raw two-dimensional (2D) spectrum that may be acquired when the IM injections are done at a high-frequency (multiplexed) injection rate but without multiplexing the TOF extractions. The x-axis represents the drift time through the IM drift tube 122, and the y-axis represents the time of flight of ions through the flight tube 138. A fundamental characteristic of IM separation is the fact that the mobilities of ions are somewhat correlated with their masses. In FIG. 3A, the distributions or grouping of signals (mass peaks) from the injections of individual ion packets into the IM drift tube 122 may be represented by IM "trend lines" or "bands" such as indicated at 312, 314, 316 and 318. Each IM band may be considered as enveloping the mass peaks (not specifically shown) acquired from a respective single injection. IM pulses may be produced at a frequency that is, for example, ten times higher than the inverse of the drift time of a given ion packet through the IM drift tube 122. During this multiplexing or "oversampling," multiple IM bands are observed in the 2D spectrum as illustrated in FIG. 3A, with each IM band corresponding to an individual ion packet that has been injected into the IM drift tube 122.

In FIG. 3A a moment of time $T_0$, also projected as a thin vertical strip or line 330, is arbitrarily positioned along the x-axis. The time $T_0$ may, for purposes of the present discussion, be considered as corresponding to the first extraction pulse implemented by the ion pulser 134 of the TOF MS 114. Thus at time $T_0$ a certain selection of ions are present in the ion pulser 134. Due to multiplexing the IM injections, ions from several IM bands 312, 314, 316 and 318 (each IM band through which the vertical strip 330 crosses) are included in the extraction occurring at time $T_0$. If a conventional "pulse and wait" approach were implemented, the second extraction ($T_1$) would occur only after all the ions reach the detector 142, and the duty cycle of the system would be very low.

Figure 3B:
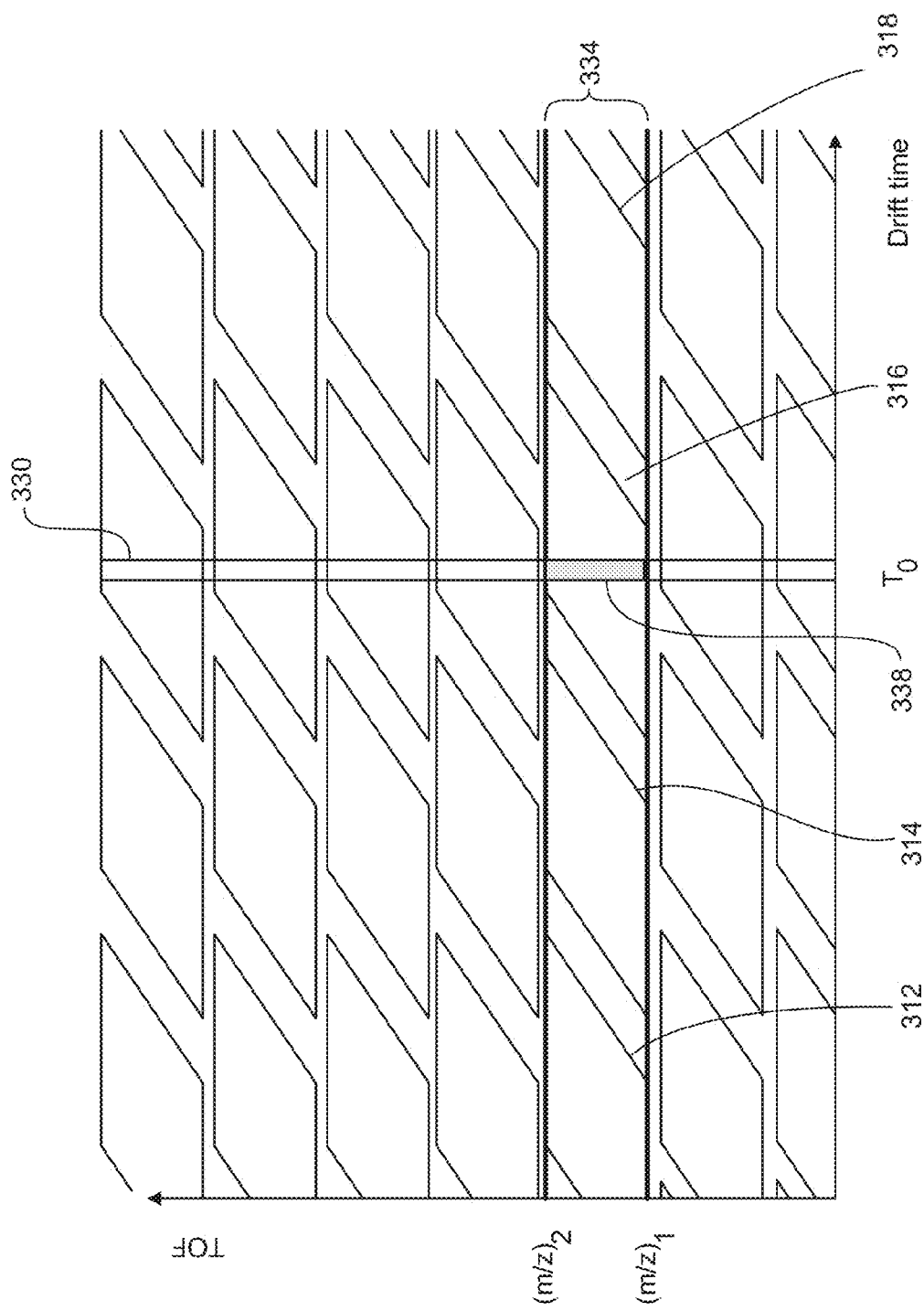
FIG. 3B is an example of a raw two-dimensional (2D) spectrum that may be acquired when multiplexing both IM injections and TOF extractions, in conjunction with implementing a mode of operation described herein.

As previously noted the duty cycle can be improved by multiplexing (overpulsing) the TOF MS 114. FIG. 3B is an example of a raw two-dimensional (2D) spectrum that may be acquired when multiplexing both IM injections and TOF extractions. Due to the multiplexed extraction rate, the data represented by the individual IM bands (e.g., bands 312, 314, 316, 318) are replicated multiple times along the vertical dimension (the time scale for TOF), whereby the data fills in the 2D space to an even greater degree than shown in FIG. 3A. Conventionally, multiplexing both IM injections and TOF extractions may lead to several disadvantages. In conventional methods, the arrival times of various ion packets at the TOF detector would overlap significantly, thereby requiring special deconvolution techniques. This is further complicated by the fact that the resolution of IM separation may be high, such that the intensity of the ion signal may vary considerably during one or several TOF extraction pulses, which makes complex deconvolution less reliable. Moreover, as previously noted complex deconvolution may require very significant real-time computational resources because IM deconvolution due to multiplexing the IM spectrometer 108 is also occurring at the same time. This level of deconvolution may be neither feasible nor practicable.

The presently disclosed method enables the use of multiplexing both the IM injections and the TOF extractions to increase the duty cycle of an IM-TOF MS system while maximizing analysis sensitivity and simplifying data acquisition. The presently disclosed method accomplishes this by acquiring spectral data from only a limited m/z range of the original ensemble of ions contained in each ion packet injected into the system. The m/z range is limited by mass filtering the ions before they are accelerated into the flight tube 138 of the TOF MS 114 as described above in conjunction with FIG. 1, or after they are accelerated into the flight tube 138 as described below in conjunction with FIG. 6.

FIG. 3B illustrates the effect of mass filtering the ion packets to a selected m/z range $(m/z)_1$ to $(m/z)_2$ while multiplexing both the IM injections and the TOF extractions. The selected m/z range $(m/z)_1$ to $(m/z)_2$ may be, as examples, 30 to 50, 50 to 100, 200 to 275, etc. More generally, the m/z range selected for a given experiment will depend on the composition and overall m/z range of the analyte ions known or suspected to be contained in the sample under analysis, and in turn on the desire to minimize or eliminate overlap between ion packets in the TOF MS 114. For instance, a narrower m/z range may be more effective for lighter ions, whereas a wider m/z range may be more effective for heavier ions. Selecting a more narrow m/z range will allow operation at a higher multiplexing rate (frequency) while avoiding (or at least minimizing) overlap of ion packets in the flight tube 138. In FIG. 3B, a horizontal region 334 represents the width (or isolation window) of the selected m/z range $(m/z)_1$ to $(m/z)_2$ over time. In the present embodiment, the width is maintained constant over time. The extension of the horizontal region 334 through all IM bands indicates that all ion packets are subjected to the same mass filtering parameters in the present embodiment. That is, each ion packet upon exiting the mass filter 112 is limited to the same m/z range $(m/z)_1$ to $(m/z)_2$ as the other ion packets when they exit the mass filter 112. Again taking time $T_0$ as a time of extraction from the ion pulser 134, the only ions that are extracted are those whose masses would be represented within a region 338 where the vertical strip 330 and the horizontal region 334 intersect. At the position chosen for time $T_0$ in FIG. 3B, the region 338 overlays a single IM band 316 and does not overlap with any other IM band 312, 314, 318 available at time $T_0$. Consequently, at this particular time $T_0$ the m/z range $(m/z)_1$ to $(m/z)_2$ contains ions that belong to only one IM band 316 and ions from the other IM bands 312, 314, 318 will not be transmitted into the flight tube 138.

The implementation of mass filtering as described herein enables multiplexing of the TOF MS 114 at an extraction rate (frequency) that is high enough to significantly enhance the detection of ions (within the selected m/z range) and thus increase sensitivity, yet low enough to prevent or at least significantly minimize overlap between sequential ion packets in the TOF flight tube 138. This in turn eliminates or at least significantly reduces overlapping of peaks in the resulting TOF spectrum, thereby simplifying the process of generating the mass spectrum in a given experiment. For example, for many experiments deconvolution of the TOF spectrum is no longer required. In the context of the present disclosure, "minimizing" overlap between sequential ion packets means reducing the overlap to such a degree that deconvolution of the TOF spectrum is not required in a given IM-TOF experiment. As will be appreciated by persons skilled in the art, the degree to which overlap needs to be reduced to avoid TOF deconvolution will depend on the particular experiment to be performed (e.g., the sample composition, the ionization technique utilized, the ionization conditions, or the like). Moreover, "minimizing" overlap not only encompasses reducing the overlap such that there is still a small amount of overlap, but also encompasses eliminating overlap entirely (i.e., such that there is no overlap at all between sequential ion packets in the TOF flight tube 138). Mass filtering, as implemented in accordance with the methods disclosed herein, makes available a wide range of potentially optimal extraction rates that satisfy the foregoing conditions (increasing sensitivity and minimizing overlap). Moreover, the range of optimal ion extraction rates will be wide for a wide variety of samples of interest, from small molecules to high-molecular-weight biopolymers.

Figure 4:
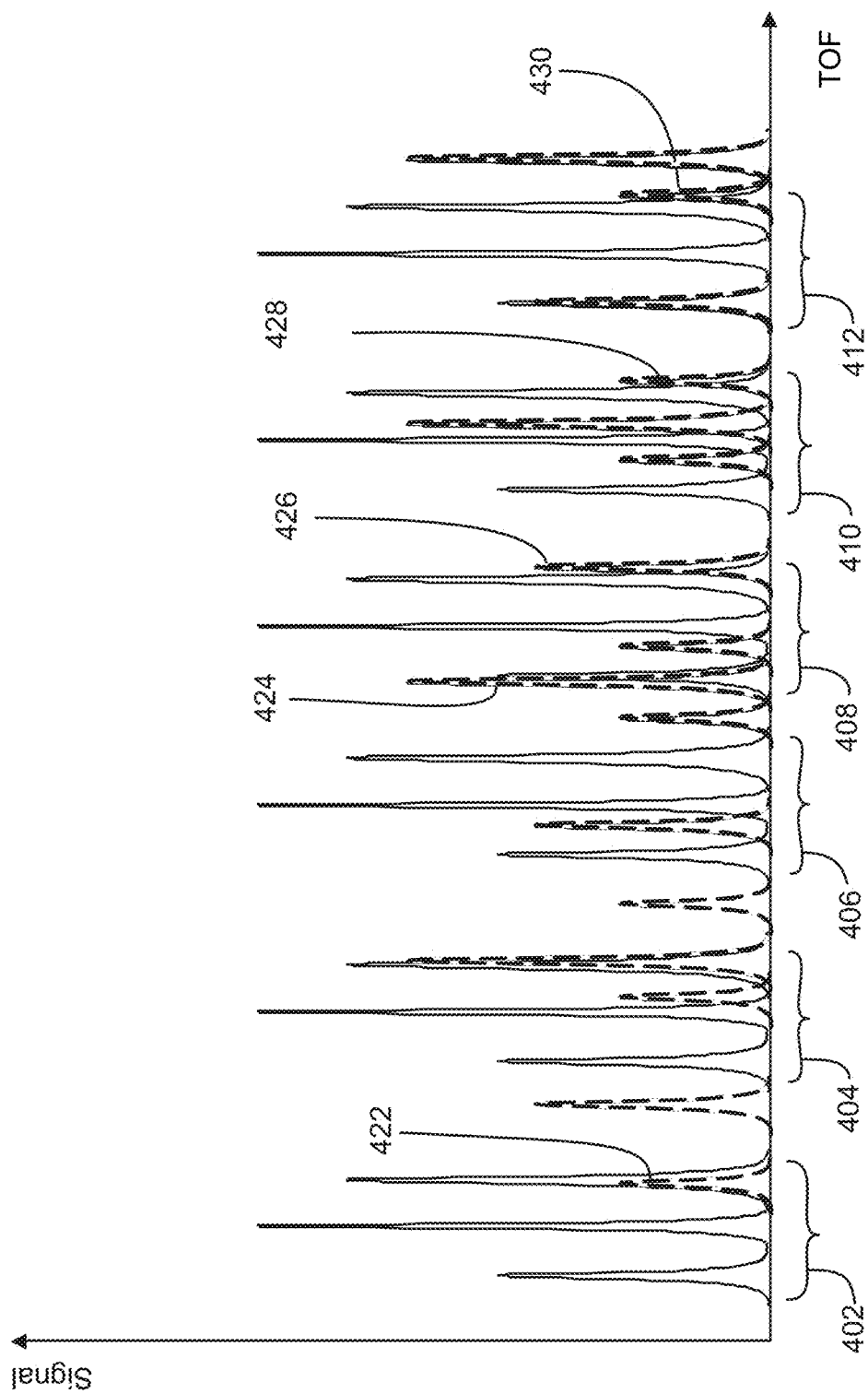
FIG. 4 is an example of a TOF spectrum that may be acquired as a result of operating the IM-TOF MS with mass filtering in accordance with modes of operation described herein.

FIG. 4 is an example of a TOF spectrum that may be acquired as a result of operating the IM-TOF MS system 100 with mass filtering in accordance with the present embodiment. The x-axis represents a series of sequential TOF acquisition cycles in microseconds, and the y-axis represents ion signal intensity in arbitrary units, resulting in a series of TOF spectra 402-412 acquired from each extracted ion packet. For simplicity, only six TOF spectra 402-412 are shown. Without multiplexing, only one of the TOF spectra 402-412 would be observed for each ion packet injected into the IM drift tube 122. FIG. 4 illustrates an example in which no overlapping of ion packets are occurring in the flight tube 138, resulting in no overlapping of the TOF spectra 402-412. It thus can be seen that no complex deconvolution of the TOF spectra 402-412 is required, and the TOF spectra 402-412 may simply be summed utilizing an appropriate time correction. Therefore, the present embodiment enables the duty cycle of both IM and TOF acquisitions to be maximized and extremely sensitive 2D spectra to be achieved for the selected m/z range of ions.

By comparison, the dashed traces in FIG. 4 represent peaks (such as at 422-430) that would be present had the m/z range of the ion packets not been restricted. Without mass filtering, the resulting significant overlap in the TOF spectra would require complex deconvolution in order to construct a mass spectrum from the TOF acquisitions.

In the first mode of operation described above, the isolation window associated with the selected m/z range does not change but rather remains constant over the entire course of data acquisition. Another method or mode of operation will now be described in which the isolation window varies in a step-wise fashion over the course of data acquisition. This second mode applies in particular to cases where multiplexing of the IM spectrometer 108 is not required such as, for example, in the case of low-level signal acquisition where overfilling of an ion accumulation device upstream of the IM drift tube 122 will not occur.

Referring to FIG. 1, in operation according to the second mode, a single ion packet is injected into the IM drift tube 122. As the ion packet moves through the IM drift tube 122 the ions become separated as a function of ion mobility in the manner described above. The resulting IM-separated ion packet is eluted from the IM drift tube 122 and transmitted into the mass filter 112. As the IM-separated ion packet travels through the mass filter 112, the ions are isolated in accordance with a varying m/z range. That is, in this mode of operation the mass filter 112 is programmed (i.e., its operational parameters such as voltage magnitude and frequency are dynamically adjusted) by, for example, hardware and/or software modules of the system controller 118, such that the m/z range imposed by the mass filter 112 is rapidly shifted over time. For instance, the mass filter 112 may be operated to sequentially establish m/z ranges of $(m/z)_1$-$(m/z)_2$, $(m/z)_3$-$(m/z)_4$, . . . , $(m/z)_{n-1}$-$(m/z)_n$ over the entire mass spectrum of the injected ion packet, where $(m/z)_1$ corresponds to the lowest m/z ratio and $(m/z)_n$ corresponds to the highest m/z ratio. In a typical embodiment, the m/z ranges are varied in an overlapping, step-wise fashion. For example, the first m/z range $(m/z)_1$-$(m/z)_2$ may be 100-200, the second m/z range $(m/z)_3$-$(m/z)_4$ may be 104-204, the third m/z range $(m/z)_5$-$(m/z)_6$ may be 108-208, etc. Depending on the experiment, the width of each m/z range need not be constant, and the amount (in m/z units) of overlap between successive m/z ranges need not be constant. For example, the first m/z range $(m/z)_1$-$(m/z)_2$ may be 100-200, the second m/z range $(m/z)_3$-$(m/z)_4$ may be 104-224, the third m/z range $(m/z)_5$-$(m/z)_6$ may be 134-224, etc. Depending on the experiment, the successive m/z ranges need not be stepped in an overlapping fashion. For example, the first m/z range $(m/z)_1$-$(m/z)_2$ may be 100-200, the second m/z range $(m/z)_3$-$(m/z)_4$ may be 201-301, the third m/z range $(m/z)_5$-$(m/z)_6$ may be 302-402, etc. In all such cases, as in the case of the first mode of operation, the width of the isolation window defining each iteration of limited m/z range may be on the order of tens to several hundreds, i.e., the width a given selected m/z range may range from 10 to several hundreds. As in the case of the first mode of operation, the width of the isolation windows will depend on the composition and overall m/z range of the analyte ions known or suspected to be contained in the sample under analysis (e.g., light ions versus heavy ions) so as to minimize or eliminate overlap between ion packets in the TOF MS 114.

In the examples of varying the m/z range just described, each successive m/z range is a higher m/z range than the preceding m/z range. Alternatively, the m/z range may be varied such that each successive m/z range is a lower m/z range than the preceding m/z range. More generally, the m/z range may be varied such that each successive m/z range is a different m/z range than the preceding m/z range. The most appropriate manner by which to vary the m/z range may depend on the particular experiment to be performed.

In all of the foregoing examples of varying mass isolation, the ion packet retains its IM-based separation after transmission through the mass filter 112, but now is also mass filtered in accordance with the varying m/z range. Thus, the most mobile ions of the ion packet (those at the front of the IM-separated ion packet) reach the mass filter 112 first and are filtered by the cut-off limits of the first m/z range $(m/z)_1$-$(m/z)_2$. The most mobile ions are followed in time by ions of successively lower mobilities, which are filtered by the cut-off limits of the successive intermediate m/z ranges. The least most mobile ions of the ion packet (those at the rear of the IM-separated ion packet) reach the mass filter 112 last and are filtered by the cut-off limits of the m/z range being applied by the mass filter 112 at that particular time. Depending on the experiment, the least most mobile ions may be filtered by the cut-off limits of the last m/z range $(m/z)_{n-1}$-$(m/z)_n$ that the mass filter 112 is programmed to apply.

As the IM-separated, mass filtered ion packet is transmitted from the mass filter 112 into the ion pulser 134, the ion pulser 134 sequentially extracts ions from the ion packet arriving in the ion pulser 134, thereby sequentially accelerating "new" ion packets into the flight tube 138. As in the case of the first mode of operation, the extraction or pulse rate (or frequency) is a multiplexed extraction rate. As each extracted ion packet travels through the flight tube 138 the ion packet becomes spatially and temporally dispersed in accordance with differing velocities. The detector 142 counts the ions as they arrive at the detector 142 and produces an ion detection signal from which TOF spectra and ultimately a mass spectrum can be generated.

As in the case of the first mode of operation, the limits imposed by the mass filtering applied to the ion packets consequently limits the dispersion or spread of the extracted ion packets such that little or no overlap among sequential ion packets occurs in the flight tube 138. That is, overlap is "minimized" as described above. As noted above, this enables the TOF MS 114 to be multiplexed and consequently to increase sensitivity, and data acquisition is significantly simplified so as to eliminate the need for deconvolution of the TOF spectrum. The effect of applying varied mass filtering in accordance with the second mode of operation is described below in conjunction with FIGS. 5A and 5B.

Figure 5A:
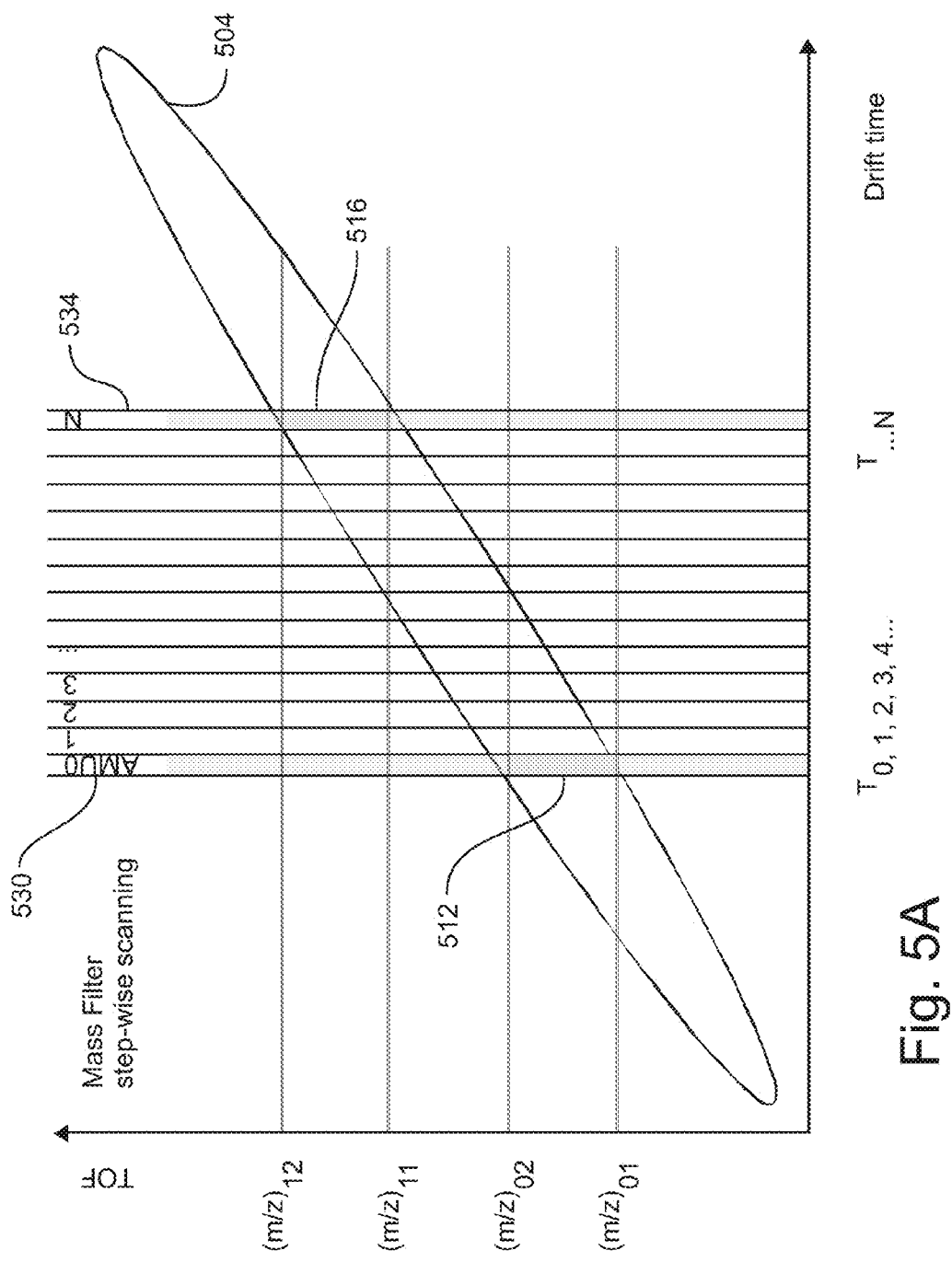
FIG. 5A is an example of a raw two-dimensional (2D) spectrum that may be acquired from a single injection into the IM drift tube and without multiplexing the TOF extractions.

FIG. 5A is an example of a raw two-dimensional (2D) spectrum that may be acquired from a single injection into the IM drift tube 122 and without multiplexing the TOF extractions. The x-axis represents the drift time of the ions through the IM drift tube 122, and the y-axis represents the time of flight of the ions through the flight tube 138. A single IM band 504 in FIG. 5 represents the injection of a single ion packet into the IM drift tube 122. For purposes of the present discussion, the times $T_0, T_1, \ldots T_N$ may be considered to correspond to the elution times of ions of the ion packet into the mass filter 112 from the IM drift tube 122. The times $T_0, T_1, \ldots T_N$ are also projected as thin vertical strips along the TOF time scale, including a strip 530 at time $T_0$ and a strip 534 at time $T_N$. At time $T_0$, the mass filter 112 is set to transmit ions in a first m/z range $(m/z)_{01}$-$(m/z)_{02}$. At subsequent times $T_1, T_2, T_3, \ldots$, the mass filter 112 is set to transmit ions in successively higher m/z ranges, leading to time $T_N$ at which the mass filter 112 is set to transmit ions in a m/z range $(m/z)_{11}$-$(m/z)_{12}$. At any given time T, the mass filter 112 is programmed to transmit m/z ranges corresponding to the appropriate location of the ions in the IM band 504. The step-wise changes in the settings of the mass filter 112 are performed frequently enough that the m/z window (iterative m/z ranges) closely follows the shape and direction of the IM band 504 as it proceeds through the IM-TOF MS system 100. This process is partially depicted in FIG. 5A by a region 512 at which the m/z range $(m/z)_{01}$-$(m/z)_{02}$ intersects time $T_0$ and a region 516 at which the m/z range $(m/z)_{11}$-$(m/z)_{12}$ intersects time $T_N$. Both regions 512 and 516 fall within the IM band 504. Once the m/z ranges are pre-selected, the maximum multiplexing frequency is determined which allows one to avoid (or at least minimize) overlap between successive ion packets in the flight tube 138. Alternatively, more narrow m/z ranges may be selected which would allow one to operate at a higher multiplexing frequency. This approach would lead to an even higher efficiency of detection, but only for a sub-population of ions arriving into the pulser region.

Figure 5B:
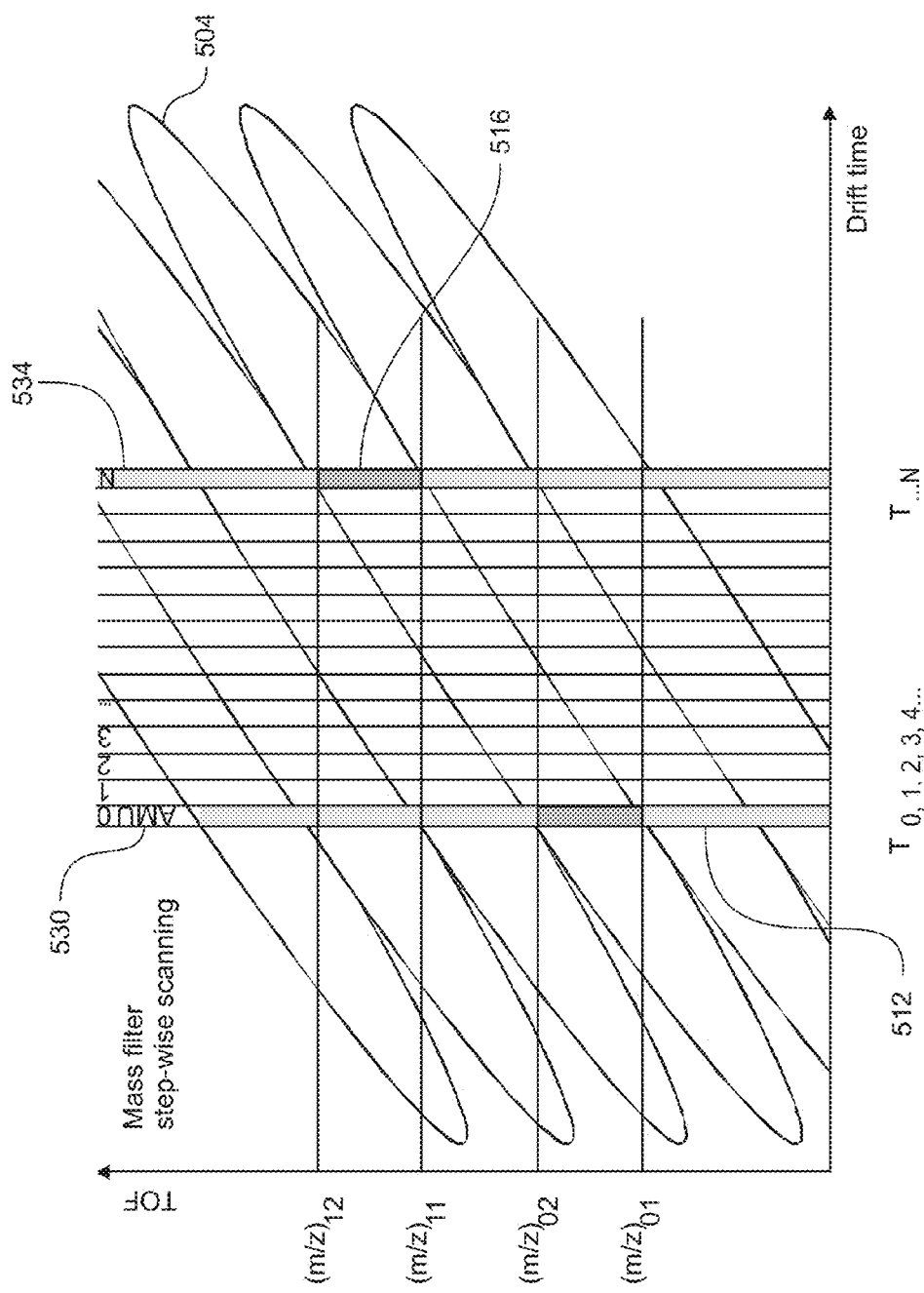
FIG. 5B is an example of a raw two-dimensional (2D) spectrum that may be acquired from a single injection into the IM drift tube when multiplexing TOF extractions, in conjunction with implementing a mode of operation described herein.

FIG. 5B is an example of a raw two-dimensional (2D) spectrum that may be acquired from a single injection into the IM drift tube when multiplexing TOF extractions. Due to the multiplexed extraction rate, the data represented by the single IM band 504 is replicated multiple times along the vertical dimension (the time scale for TOF), whereby the data fills in the 2D space to a much greater degree than shown in FIG. 5A. By example, FIG. 5B shows five copies of the IM band 504, representing six TOF extractions. Because multiple TOF extractions are taken from each portion of the eluted ion packet (each portion roughly corresponding to the elution times $T_0, T_1, \ldots T_N$), data is collected from the entire 2D space that is available at each time. For example, at time $T_0$, data is collected not only from the single region 512 but also from the other regions of the overall vertical strip 530. Stated another way, at time $T_0$ the data acquired from the first TOF extraction may correspond to region 512, and the data acquired from the next TOF extraction (occurring a very short time after the first TOF extraction) may correspond to the region of the vertical strip 530 directly above the region 512, and so on. Subsequently, multiple TOF extractions are repeated for the remaining portions of the ion packet (i.e., the remaining elution times $T_1, T_2, T_3, \ldots T_N$). In this manner, data is acquired from the ion packet over the entire 2D space made available through multiplexing the TOF extractions. While this process is occurring, the m/z range is varied in a step-wise in the manner described above in conjunction with FIG. 5A. In this manner, all of the ions of the injected ion packet may be acquired, and sensitivity is enhanced not just in one limited m/z range but over the entire spectrum of the sample of interest.

Moreover, mass filtering may be utilized to eliminate non-analytical background ions (such as may be produced from contaminants or solvent matrix) from the mass spectrum. The background ions typically have a broader distribution in the 2D space and their distribution does not follow the IM bands.

The method implementing the second mode of operation may be repeated for additional ion packets, with each ion packet being injected into the IM drift tube 122 one ion packet at a time.

FIG. 6 is a schematic view of another example of a hybrid IM-TOF MS system 200 that may be utilized in the implementation of methods described herein, including the modes of mass filtering described above. In this embodiment, the mass filter 112 is positioned in the flight tube 138 of the TOF MS 114 instead of between the IM drift tube 122 and the TOF MS 114. The mass filter 112 may have any suitable configuration such as described above by example in conjunction with FIG. 1. When the mass filter 112 is positioned as shown in FIG. 6, a Bradbury-Nielsen gate or similar ion optics device is presently contemplated as being the more typical embodiment. The Bradbury-Nielsen gate (or similar device) typically includes a set of parallel wires (or an array of wires arranged as a grid) lying in the plane orthogonal to the flight of ions (ion flight path 150). As appreciated by persons skilled in the art, a pulsed, high-frequency voltage is applied 180 degrees out of phase to alternating wires. The pulsed voltage is applied at a timing such that only ions in the selected m/z range that are passing through the wires during a certain time when the gate is "open" are able to continue along the ion flight path. Ions outside the selected m/z range pass through the wires during a different time period when the gate is "closed" such that the ions are deflected away from the ion flight path, as depicted by example at 604.

Figure 7:
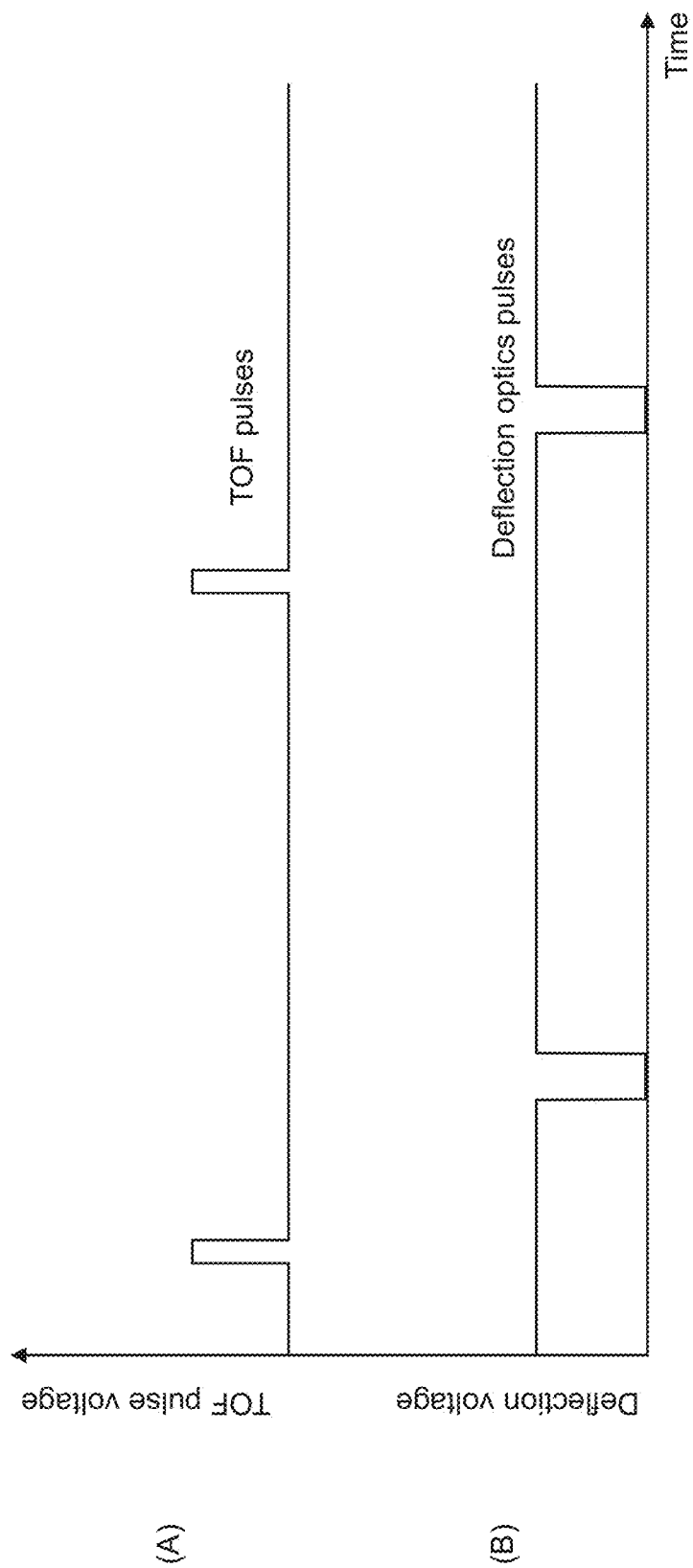
FIG. 7 illustrates typical timing sequences for (A) the TOF voltage applied to an ion pulser of the IM-TOF MS illustrated in FIG. 6, and (B) the deflection voltage applied to a Bradbury-Nielsen gate or similar ion optics device of the IM-TOF MS illustrated in FIG. 6.

FIG. 7 illustrates typical timing sequences for (A) the TOF voltage applied to the ion pulser 134 and (B) the deflection voltage applied to the mass filter 112 when configured as a Bradbury-Nielsen gate or similar ion optics device. In this embodiment, the voltage applied to the deflection element of the mass filter 112 is normally "high," and all ions are deflected and thus do not reach the detector 142. The deflection voltage is dropped to zero when ions in the desired m/z range are traveling through the mass filter 112.

As another example of an ion optics device that may be utilized as a mass filter 112 in conjunction with the methods described herein, a set of parallel deflection plates may be provided, which deflect ions when an appropriate potential difference is applied between them. More generally, the ion optics device may include any electrode geometry that can be configured for preventing the transmission of ions only during specified time intervals.

In operation, IM-separated ion packets are transmitted into the ion pulser 134 of the TOF MS 114 without mass filtering. Instead, ion packets are mass filtered after they are extracted by the ion pulser 134 into the flight tube 138 and while the ions start to become separated, as evident from FIGS. 6 and 7. In this embodiment, the mass filter 112 is located at a position after the ion pulser 134 where the ions from one extracted ion packet are sufficiently separated to facilitate mass filtering but are not yet separated enough to overlap with ions from other ion packets. As in the case of the embodiment described above in conjunction with FIG. 1, the mass filtering of the ions limits their dispersion or spread such that little or no overlap among sequential ion packets occurs in the flight tube 138, again greatly simplifying data acquisition and analysis.

The embodiment just described and illustrated in FIGS. 6 and 7 may be utilized to implement either of the first and second modes of operation. When the mass filter 112 is located just "downstream" of the ion pulser 134 as in FIG. 6, the time $T_0$ shown in FIGS. 3A and 3B (first mode of operation) may be considered as corresponding to a time shortly after extraction, when the ions of an extracted ion packet are just starting to become separated and encounter the mass filter 112 located in the flight tube 138. Alternatively, when implementing the second mode of operation illustrated in FIGS. 5A and 5B, the TOF-positioned mass filter 112 shown in FIG. 6 may be programmed to vary the range of ion mass isolation over time in accordance with any of the step-wise mass filtering schemes described above.

Exemplary Embodiments

Exemplary embodiments provided in accordance with the presently disclosed subject matter include, but are not limited to, the following:

1. A method for acquiring spectrometric data from ions, the method comprising:

injecting a plurality of ion packets sequentially into an ion mobility (IM) drift tube at a multiplexed injection rate, such that at least two injected ion packets are present in the IM drift tube at the same time;

separating ions in each injected ion packet according to IM as the ions drift through the IM drift tube to produce a plurality of IM-separated ion packets from the respective injected ion packets;

transmitting the IM-separated ion packets into a mass filter to produce a plurality of mass-filtered ion packets, each mass-filtered ion packet comprising ions of the same selected m/z range as the ions of the other mass-filtered ion packets;

transmitting the mass-filtered ion packets into a pulser of a time-of-flight (TOF) mass spectrometer;

extracting a plurality of ion packets sequentially from the pulser into a flight tube of the TOF mass spectrometer to produce a plurality of extracted ion packets from the mass-filtered ion packets, wherein extraction is performed at a multiplexed extraction rate such that more than one extracted ion packet is produced from the same mass-filtered ion packet and at least two extracted ion packets are present in the flight tube at the same time;

separating ions in each extracted ion packet according to TOF as the ions drift through the flight tube to produce a plurality of TOF-separated ion packets in the flight tube from the respective extracted ion packets; and detecting ions of the TOF-separated ion packets as the ions arrive at a detector of the TOF mass spectrometer.

2. A method for acquiring spectrometric data from ions, the method comprising:

injecting a plurality of ion packets sequentially into an ion mobility (IM) drift tube at a multiplexed injection rate, such that at least two injected ion packets are present in the IM drift tube at the same time;

separating ions in each injected ion packet according to IM as the ions drift through the IM drift tube to produce a plurality of IM-separated ion packets from the respective injected ion packets;

transmitting the IM-separated ion packets into a pulser of a time-of-flight (TOF) mass spectrometer;

extracting a plurality of ion packets sequentially from the pulser into a flight tube of the TOF mass spectrometer to produce a plurality of extracted ion packets from the IM-separated ion packets, wherein extraction is performed at a multiplexed extraction rate such that more than one extracted ion packet is produced from the same IM-separated ion packet and at least two extracted ion packets are present in the flight tube at the same time;

separating ions in each extracted ion packet according to TOF as the ions drift through the flight tube to produce a plurality of TOF-separated ion packets in the flight tube from the respective extracted ion packets;

while separating the ions in each extracted ion packet, transmitting the extracted ion packets into a mass filter to produce a plurality of mass-filtered ion packets, each mass-filtered ion packet comprising ions of the same selected m/z range as the ions of the other mass-filtered ion packets; and detecting ions of the mass-filtered ion packets as the ions arrive at a detector of the TOF mass spectrometer.

3. A method for acquiring spectrometric data from ions, the method comprising:

injecting an ion packet into an ion mobility (IM) drift tube;

separating ions in the injected ion packet according to IM as the ions drift through the IM drift tube to produce an IM-separated ion packet in the IM drift tube;

transmitting the IM-separated ion packet into a mass filter;

while transmitting the IM-separated ion packet into the mass filter, isolating first ions of a first m/z range and transmitting the first ions into a pulser of a time-of-flight (TOF) mass spectrometer;

while transmitting the first ions into the pulser, extracting a plurality of ion packets of the first ions sequentially from the pulser into a flight tube of the TOF mass spectrometer at a multiplexed extraction rate, such that at least two extracted ion packets of the first ions are present in the flight tube at the same time;

while transmitting the IM-separated ion packet into the mass filter, and after isolating the first ions, isolating second ions of a second m/z range higher the first m/z range and transmitting the second ions into the pulser;

while transmitting the second ions into the pulser, extracting a plurality of ion packets of the second ions sequentially into the flight tube at a multiplexed extraction rate, such that at least two extracted ion packets of the second ions are present in the flight tube at the same time;

separating ions in each extracted ion packet of the first ions and each extracted ion packet of the second ions according to TOF as the ions drift through the flight tube, to produce a plurality of TOF-separated ion packets in the flight tube from the respective extracted ion packets; and detecting ions of the TOF-separated ion packets as the ions arrive at a detector of the TOF mass spectrometer.

4. A method for acquiring spectrometric data from ions, the method comprising:
injecting an ion packet into an ion mobility (IM) drift tube;
separating ions in the injected ion packet according to IM as the ions drift through the IM drift tube to produce an IM-separated ion packet in the IM drift tube;
transmitting the IM-separated ion packet into a pulser of a time-of-flight (TOF) mass spectrometer;
while transmitting the first ions into the pulser, extracting a plurality of ion packets of the first ions sequentially from the pulser into a flight tube of the TOF mass spectrometer at a multiplexed extraction rate, such that at least two extracted ion packets are present in the flight tube at the same time;
isolating first ions of a first m/z range to produce a plurality of extracted ion packets of first ions;
after isolating the first ions, isolating second ions of a second m/z range higher the first m/z range to produce a plurality of extracted ion packets of second ions;
separating ions in each extracted ion packet of the first ions and each extracted ion packet of the second ions according to TOF as the ions drift through the flight tube, to produce a plurality of TOF-separated ion packets in the flight tube from the respective extracted ion packets; and
detecting ions of the TOF-separated ion packets as the ions arrive at a detector of the TOF mass spectrometer.

5. An IM-TOF MS system configured for performing the method of any one of the preceding embodiments.

6. A computer-readable storage medium comprising instructions for performing the method of any one of the preceding embodiments.

7. An IM-TOF MS system comprising the computer-readable storage medium of embodiment 6.

8. An IM-TOF MS system, comprising:
an IM drift tube;
a TOF MS comprising a TOF flight tube positioned to receive ions eluted from the IM drift tube, a pulser, a detector, and an electric field-free drift region defining an ion flight path between the pulser and the detector; and
a mass filter configured for selecting ions for transmission within an adjustable m/z range, wherein the mass filter is positioned between the IM drift tube and the TOF flight tube, or is positioned in the TOF flight tube downstream of the pulser.

9. A method for acquiring spectrometric data from ions, the method comprising:
injecting a plurality of ion packets sequentially into an ion mobility (IM) drift tube at a multiplexed injection rate, such that at least two ion packets are present in the IM drift tube at the same time;
separating ions in each ion packet according to IM as the ions drift through the IM drift tube;
transmitting the ion packets into a pulser of a time-of-flight (TOF) mass spectrometer;
extracting a plurality of new ion packets sequentially from the pulser into a flight tube of the TOF mass spectrometer, wherein extraction is performed at a multiplexed extraction rate such that more than one extracted ion packet is produced from the same ion packet transmitted into the pulser, and at least two extracted ion packets are present in the flight tube at the same time;
separating ions in each extracted ion packet according to TOF as the ions drift through the flight tube;
detecting ions as the ions arrive at a detector from the flight tube; and
before detecting the ions, selecting ions only of a specific m/z range, wherein each ion packet in the flight tube comprises ions of the same selected m/z range as the ions of the other ion packets, and overlap between sequential ion packets in the flight tube is minimized.

10. The method of embodiment 9, wherein the specific m/z range has a width ranging from ten to several hundreds.

11. A method for acquiring spectrometric data from ions, the method comprising:
injecting a plurality of ion packets sequentially into an ion mobility (IM) drift tube at a multiplexed injection rate, such that at least two ion packets are present in the IM drift tube at the same time;
separating ions in each ion packet according to IM as the ions drift through the IM drift tube;
transmitting the ion packets into a pulser of a time-of-flight (TOF) mass spectrometer;
extracting a plurality of new ion packets sequentially from the pulser into a flight tube of the TOF mass spectrometer, wherein extraction is performed at a multiplexed extraction rate such that more than one extracted ion packet is produced from the same ion packet transmitted into the pulser, and at least two extracted ion packets are present in the flight tube at the same time;
separating ions in each extracted ion packet according to TOF as the ions drift through the flight tube;
detecting ions as the ions arrive at a detector from the flight tube; and
before detecting the ions, selecting ions only of a specific m/z range, wherein each ion packet in the flight tube comprises ions of the same selected m/z range as the ions of the other ion packets, and the specific m/z range has a width ranging from ten to several hundreds.

12. A method for acquiring spectrometric data from ions, the method comprising:
injecting an ion packet into an ion mobility (IM) drift tube;
separating ions in the ion packet according to IM as the ions drift through the IM drift tube;
transmitting the ion packet into a pulser of a time-of-flight (TOF) mass spectrometer;
extracting a plurality of new ion packets sequentially from the pulser into a flight tube of the TOF mass spectrometer, wherein extraction is performed at a multiplexed extraction rate such that more than one extracted ion packet is produced from the same ion packet transmitted into the pulser, and at least two extracted ion packets are present in the flight tube at the same time;
separating ions in each extracted ion packet according to TOF as the ions drift through the flight tube;
detecting ions of the TOF-separated ion packets as the ions arrive at a detector of the TOF mass spectrometer; and
before detecting the ions, selecting ions in successive m/z ranges, wherein each successive m/z range is a different m/z range than the preceding m/z range, and each m/z range has a width selected to minimize overlap between sequential ion packets in the flight tube.

13. The method of embodiment 12, wherein the successive m/z ranges each have a width ranging from tens to several hundreds.

14. The method of embodiment 12 or 13, wherein at least one m/z range at least partially overlaps with a preceding m/z range.

15. The method of any of embodiments 9-14, comprising producing a mass spectrum of the detected ions without requiring deconvolution of the TOF-separated ion packets.

16. The method of any of embodiments 9-15, wherein at least two adjacent IM-separated ion packets at least partially overlap in the IM drift tube, and further comprising producing a mass spectrum of the detected ions, wherein producing the mass spectrum comprises deconvoluting the IM-separated ion packets.
17. The method of any of embodiments 9-16, wherein selecting the ions comprises, after separating ions in each ion packet according to IM, transmitting the ion packets through a mass filter, and wherein the ion packets transmitted into the pulser are mass-filtered ion packets.
18. The method of any of embodiments 9-16, wherein selecting the ions comprises, after extracting the ion packets from the pulser, transmitting the ion packets through a mass filter positioned in the drift tube.
19. The method of any of embodiments 9-18, wherein selecting the ions comprises transmitting the ion packets through a mass filter selected from the group consisting of a multi-pole mass filter, an ion optics device, and a Bradbury-Nielsen gate.
20. The method of any of embodiments 12-19 comprising, after detecting the ions, repeating the steps of claim 9 for one or more addition ion packets to be injected into the drift tube.
21. The method of any of embodiments 12-20, wherein each successive m/z range is a higher m/z range than the preceding m/z range.
22. The method of any of embodiments 12-20, wherein each successive m/z range is a lower m/z range than the preceding m/z range.
23. The ion mobility time-of-flight mass spectrometer system, comprising a system controller communicating with the IM drift tube, the mass filter and the TOF mass spectrometer, and configured to perform the any of embodiments 9-22.

It will be understood that one or more of the processes, sub-processes, and process steps described herein may be performed by hardware, firmware, software, or a combination of two or more of the foregoing, on one or more electronic or digitally-controlled devices. The software may reside in a software memory (not shown) in a suitable electronic processing component or system such as, for example, the system controller 118 schematically depicted in FIGS. 1 and 6. The software memory may include an ordered listing of executable instructions for implementing logical functions (that is, "logic" that may be implemented in digital form such as digital circuitry or source code, or in analog form such as an analog source such as an analog electrical, sound, or video signal). The instructions may be executed within a processing module, which includes, for example, one or more microprocessors, general purpose processors, combinations of processors, digital signal processors (DSPs), or application specific integrated circuits (ASICs). Further, the schematic diagrams describe a logical division of functions having physical (hardware and/or software) implementations that are not limited by architecture or the physical layout of the functions. The examples of systems described herein may be implemented in a variety of configurations and operate as hardware/software components in a single hardware/software unit, or in separate hardware/software units.

The executable instructions may be implemented as a computer program product having instructions stored therein which, when executed by a processing module of an electronic system (e.g., the system controller 118 in FIG. 1), direct the electronic system to carry out the instructions. The computer program product may be selectively embodied in any non-transitory computer-readable storage medium for use by or in connection with an instruction execution system, apparatus, or device, such as a electronic computer-based system, processor-containing system, or other system that may selectively fetch the instructions from the instruction execution system, apparatus, or device and execute the instructions. In the context of this disclosure, a computer-readable storage medium is any non-transitory means that may store the program for use by or in connection with the instruction execution system, apparatus, or device. The non-transitory computer-readable storage medium may selectively be, for example, an electronic, magnetic, optical, electromagnetic, infrared, or semiconductor system, apparatus, or device. A non-exhaustive list of more specific examples of non-transitory computer readable media include: an electrical connection having one or more wires (electronic); a portable computer diskette (magnetic); a random access memory (electronic); a read-only memory (electronic); an erasable programmable read only memory such as, for example, flash memory (electronic); a compact disc memory such as, for example, CD-ROM, CD-R, CD-RW (optical); and digital versatile disc memory, i.e., DVD (optical). Note that the non-transitory computer-readable storage medium may even be paper or another suitable medium upon which the program is printed, as the program can be electronically captured via, for instance, optical scanning of the paper or other medium, then compiled, interpreted, or otherwise processed in a suitable manner if necessary, and then stored in a computer memory or machine memory.

It will also be understood that the term "in signal communication" as used herein means that two or more systems, devices, components, modules, or sub-modules are capable of communicating with each other via signals that travel over some type of signal path. The signals may be communication, power, data, or energy signals, which may communicate information, power, or energy from a first system, device, component, module, or sub-module to a second system, device, component, module, or sub-module along a signal path between the first and second system, device, component, module, or sub-module. The signal paths may include physical, electrical, magnetic, electromagnetic, electrochemical, optical, wired, or wireless connections. The signal paths may also include additional systems, devices, components, modules, or sub-modules between the first and second system, device, component, module, or sub-module.

More generally, terms such as "communicate" and "in . . . communication with" (for example, a first component "communicates with" or "is in communication with" a second component) are used herein to indicate a structural, functional, mechanical, electrical, signal, optical, magnetic, electromagnetic, ionic or fluidic relationship between two or more components or elements. As such, the fact that one component is said to communicate with a second component is not intended to exclude the possibility that additional components may be present between, and/or operatively associated or engaged with, the first and second components.

It will be understood that various aspects or details of the invention may be changed without departing from the scope of the invention. Furthermore, the foregoing description is for the purpose of illustration only, and not for the purpose of limitation—the invention being defined by the claims.

What is claimed is:
1. A method for acquiring spectrometric data from ions, the method comprising:
   injecting a plurality of ion packets sequentially into an ion mobility (IM) drift tube at a multiplexed injection rate, such that at least two ion packets are present in the IM drift tube at the same time;
   separating ions in each ion packet according to IM as the ions drift through the IM drift tube;

transmitting the ion packets into a pulser of a time-of-flight (TOF) mass spectrometer;

extracting a plurality of new ion packets sequentially from the pulser into a flight tube of the TOF mass spectrometer, wherein extraction is performed at a multiplexed extraction rate such that more than one extracted ion packet is produced from the same ion packet transmitted into the pulser, and at least two extracted ion packets are present in the flight tube at the same time;

separating ions in each extracted ion packet according to TOF as the ions drift through the flight tube;

detecting ions as the ions arrive at a detector from the flight tube; and before detecting the ions, selecting ions only of a specific m/z range, wherein each ion packet in the flight tube comprises ions of the same selected m/z range as the ions of the other ion packets, and overlap between sequential ion packets in the flight tube is minimized.

2. The method of claim 1, wherein the specific m/z range has a width ranging from ten to several hundreds.

3. The method of claim 1, comprising producing a mass spectrum of the detected ions without requiring deconvolution of the TOF-separated ion packets.

4. The method of claim 1, wherein at least two adjacent IM-separated ion packets at least partially overlap in the IM drift tube, and further comprising producing a mass spectrum of the detected ions, wherein producing the mass spectrum comprises deconvoluting the IM-separated ion packets.

5. The method of claim 1, wherein selecting the ions comprises, after separating ions in each ion packet according to IM, transmitting the ion packets through a mass filter, and wherein the ion packets transmitted into the pulser are mass-filtered ion packets.

6. The method of claim 1, wherein selecting the ions comprises, after extracting the ion packets from the pulser, transmitting the ion packets through a mass filter positioned in the drift tube.

7. The method of claim 1, wherein selecting the ions comprises transmitting the ion packets through a mass filter selected from the group consisting of a multi-pole mass filter, an ion optics device, and a Bradbury-Nielsen gate.

8. An ion mobility time-of-flight mass spectrometer system, comprising a system controller communicating with the IM drift tube, the mass filter and the TOF mass spectrometer, and configured to perform the method of claim 1.

9. A method for acquiring spectrometric data from ions, the method comprising:

injecting an ion packet into an ion mobility (IM) drift tube;

separating ions in the ion packet according to IM as the ions drift through the IM drift tube;

transmitting the ion packet into a pulser of a time-of-flight (TOF) mass spectrometer;

extracting a plurality of new ion packets sequentially from the pulser into a flight tube of the TOF mass spectrometer, wherein extraction is performed at a multiplexed extraction rate such that more than one extracted ion packet is produced from the same ion packet transmitted into the pulser, and at least two extracted ion packets are present in the flight tube at the same time;

separating ions in each extracted ion packet according to TOF as the ions drift through the flight tube;

detecting ions of the TOF-separated ion packets as the ions arrive at a detector of the TOF mass spectrometer; and before detecting the ions, selecting ions in successive m/z ranges, wherein each successive m/z range is a different m/z range than the preceding m/z range, and each m/z range has a width selected to minimize overlap between sequential ion packets in the flight tube.

10. The method of claim 9, wherein the successive m/z ranges each have a width ranging from tens to several hundreds.

11. The method of claim 9, wherein at least one m/z range at least partially overlaps with a preceding m/z range.

12. The method of claim 9, comprising producing a mass spectrum of the detected ions without requiring deconvolution of the TOF-separated ion packets.

13. The method of claim 9, wherein at least two adjacent IM-separated ion packets at least partially overlap in the IM drift tube, and further comprising producing a mass spectrum of the detected ions, wherein producing the mass spectrum comprises deconvoluting the IM-separated ion packets.

14. The method of claim 9, wherein selecting the ions comprises, after separating ions in each ion packet according to IM, transmitting the ion packets through a mass filter, and wherein the ion packets transmitted into the pulser are mass-filtered ion packets.

15. The method of claim 9, wherein selecting the ions comprises, after extracting the ion packets from the pulser, transmitting the ion packets through a mass filter positioned in the drift tube.

16. The method of claim 9, wherein selecting the ions comprises transmitting the ion packets through a mass filter selected from the group consisting of a multi-pole mass filter, an ion optics device, and a Bradbury-Nielsen gate.

17. The method of claim 9 comprising, after detecting the ions, repeating the steps of claim 9 for one or more addition ion packets to be injected into the drift tube.

18. The method of claim 9, wherein each successive m/z range is a higher m/z range than the preceding m/z range.

19. The method of claim 9, wherein each successive m/z range is a lower m/z range than the preceding m/z range.

20. An ion mobility time-of-flight mass spectrometer system, comprising a system controller communicating with the IM drift tube, the mass filter and the TOF mass spectrometer, and configured to perform the method of claim 9.

* * * * *